United States Patent [19]

Guerrero et al.

[11] 4,326,522

[45] Apr. 27, 1982

[54] MESH-COVERED BOLUS

[75] Inventors: Jorge Guerrero, Pennington; Alice D. Mellon, Bridgewater; Charles G. Fritz, Basking Ridge; Namassivaya Doddi, Manville, all of N.J.

[73] Assignee: Pitman-Moore, Inc., Washington Crossing, N.J.

[21] Appl. No.: 157,591

[22] Filed: Jun. 9, 1980

[51] Int. Cl.³ .............................................. A61M 7/00
[52] U.S. Cl. .................................. 128//260; 128/223
[58] Field of Search ................... 128/213 R, 222, 223, 128/260

[56] References Cited

U.S. PATENT DOCUMENTS

| 3,844,285 | 10/1974 | Laby | 128/260 |
| 3,887,699 | 6/1975 | Volles | 128/260 |
| 4,034,756 | 7/1977 | Higuchi et al. | 128/260 |
| 4,207,890 | 6/1980 | Mamajek | 128/223 |
| 4,220,152 | 9/1980 | Dresback | 128/260 |
| 4,220,153 | 9/1980 | Dresback | 128/260 |
| 4,228,149 | 10/1980 | Brewer et al. | 128/260 |

Primary Examiner—C. Fred Rosenbaum

[57] ABSTRACT

A bolus for administering medicament containing the medicament in a bio-erodible polymer having a shape or size so that it is retained in the rumen for at least two weeks, having a fine mesh completely encasing the bolus, which can contain a heavy metal core to give it weight, or can be in two segments connected by a spring, or a flexible polyurethane band, which changes position after being administered to the animal.

2 Claims, 10 Drawing Figures

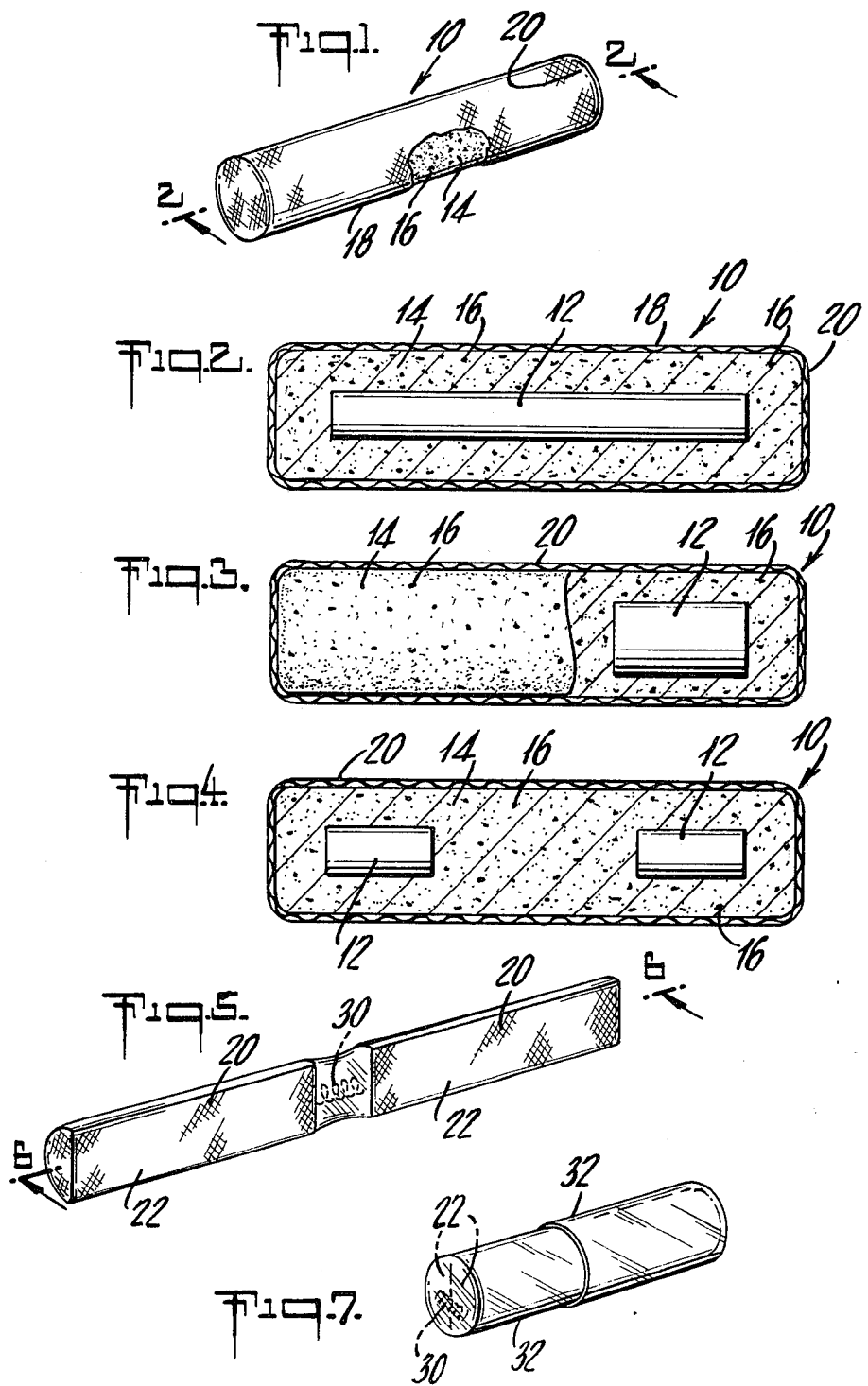

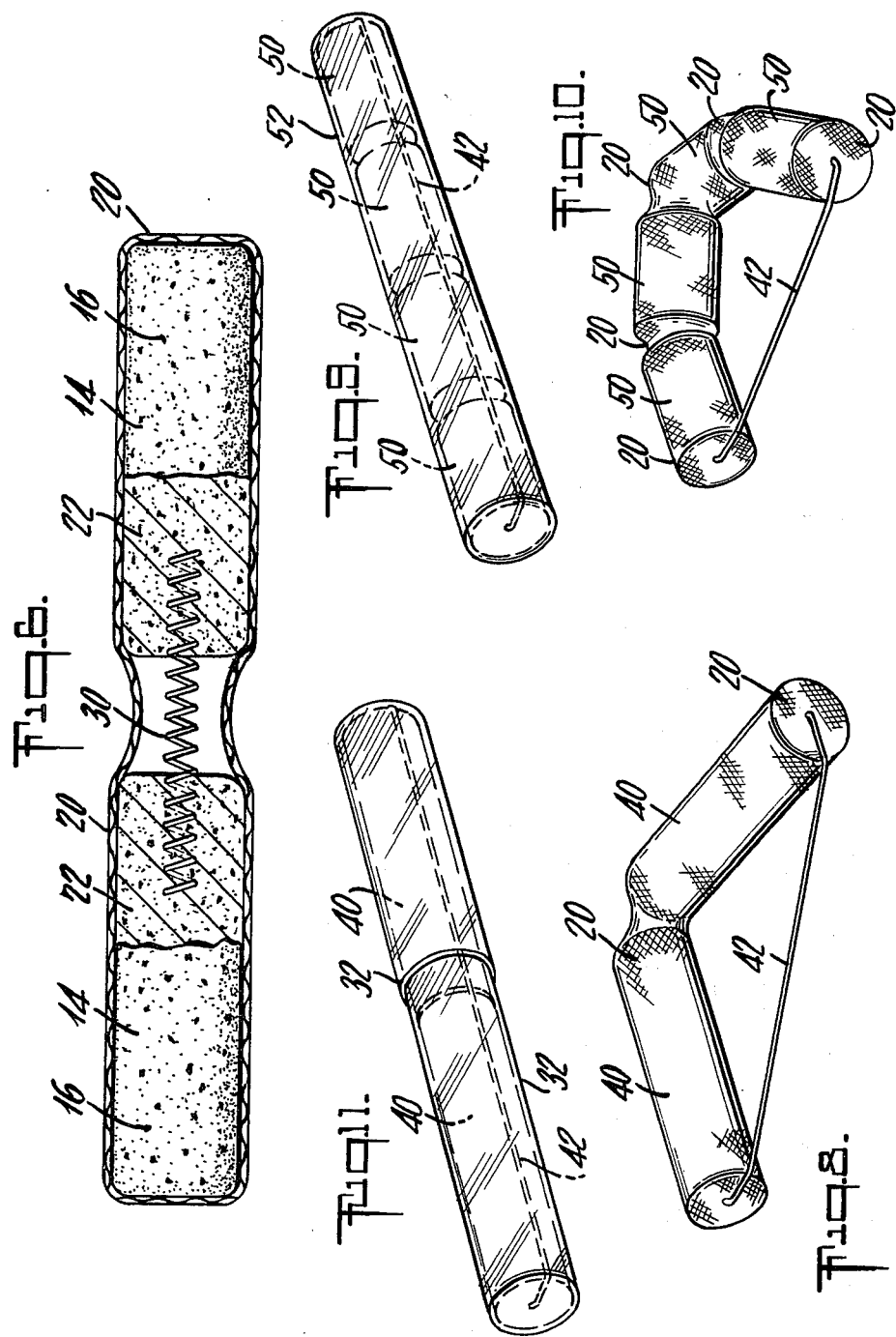

MESH-COVERED BOLUS

This invention relates to boluses for ruminants, and is more particularly concerned with a bolus which is retained in the rumen for a long period of time so that medicament can be continuously provided over a long period of time, which bolus is surrounded by a mesh to prevent pieces of medicament from breaking off and being lost.

It is well known to administer medicines orally to animals in the form of a bolus, i.e., for purposes of this patent application, a large tablet. For certain conditions, for example to treat parasites, it is desirable to have a long-acting, sustained-release medicament which will continuously provide a relatively uniform dosage over a long period of time, i.e., at least two weeks. Ruminants, the most common of which are cattle and sheep, have a complex, multi-chambered stomach, regurgitate what they swallow, chew their cuds, and spit out conventional boluses relatively quickly. It would be advantageous to provide a drug delivery device for prolongedly releasing the drug at a controlled rate in the rumen; to have said device to be easily swallowable by ruminants and be capable of administration in the same manner as boluses now in common use, i.e., with a bolling gun; to have said device rumen-retentive, i.e., to be retained in the rumen for at least two weeks without being regurgitated and lost, or otherwise eliminated from the rumen. The term rumen as used herein is intended to include the reticulum and be a synonym for the various stomachs of ruminants.

The bolus of the present invention solves these problems by providing the desired medicament admixed in a bio-erodible sustained-release matrix, which matrix is completely encased in a fine mesh made of a non-absorbable material. The boluses of the present invention contain the desired medicament (e.g., an anthelmintic) incorporated or admixed into a bio-erodible sustained-release matrix (such as an absorbable polymer) which, when dissolved in the body fluids of the rumen, will gradually erode and gradually release the medicament at the desired rate.

Each rumen-retentive bolus of the present invention can be easily administered to animals since it has a size and shape which permits it to be dispensed from a bolling gun, and which size and shape preferably is roughly on the order of commercially-available type boluses now in common use. For use with sheep, the bolus, at the point of administration, preferably would be generally in the form of a solid cylinder about 0.5 inches (1.3 centimeters) in diameter, varying in length from about 0.5 to about 2.5 inches (1.3–6.6 centimeters). For use with cattle, the bolus preferably would normally be somewhat larger, about ⅞ inches-1 inch (2.2 centimeters to 2.6 centimeters) in diameter, varying in length from about 1 to about 3 inches (2.5 to about 7.5 centimeters). It is not necessary that the cylinder be a true cylinder, and the bolus could be square or triangular or any polygon or other shape if desired, as long as it can fit in and be released by a bolling gun.

The boluses of the present invention employ retention means to prevent premature regurgitation. While they should be "bolus-shape" at the time of its administration, in order for any bolus to be rumen-retentive, it must contain sufficient size and/or weight, such as a heavy metal core element, or else its configuration should change and it should increase in dimension after reaching the rumen, so that it will not be regurgitated with the food present in the rumen.

A variety of boluses within the scope of the present invention are possible, some in one segment and some with multiple segments. The preferred bolus of the present invention is formed from two or more connected mesh-covered matrix segments, at least two of which are joined together by flexible resilient means, e.g. by an expandable, flexible connection at one end, such as a spring or an elastic band or the like. Stainless steel springs, resilient plastic strips, flexible metal bands, twisted wire cable and spring steel can be used for certain embodiments and elastomer, silicone rubber, segmented polyether polyurethane and equivalents can be used for other embodiments. Initially, the matrix segments are placed under tension to form the "bolus-shape" (similar to a large tablet) which shape is maintained by dissolvable shape holding means, i.e., by an outer covering which dissolves relatively quickly in the body fluids of the rumen, after which the tension of the flexible resilient means, i.e., the connection between the segments, changes the spatial configuration of the connected matrix segments of the bolus, which then becomes larger in length or in another dimension and thereby remains in the rumen for a long time until much of the bio-erodible matrix containing the medicament has dissolved or eroded away, so the bolus is once again of a small enough size and shape to be regurgitated. The dissolvable shape holding means include gelatin or other collagenous materials, water-soluble coatings or films, e.g., hydroxy propyl cellulose or other cellulose derivatives, paper, agar, guar, etc., with a gelatin capsule or a hydroxy propyl cellulose capsule being preferred, but the shape holding means need not completely cover the bolus and could be in the form of a band completely surrounding some, but not all, of the bolus.

The medicaments most commonly expected so to be dispensed will be anthelmintics such as mebendazole and levamisole, or other anthelmintics for example, other benzimidazoles (albendazole, cambendazole, fenbendazole, parbendazole, oxfendazole, oxybendazole, thiabendazole); organophosphates (trichlorfon); pyrazinoisoquinolines (praziquantel); piperazines, other phenyl imidazoles, carbamates, and other anthelmintics, such as morantel, pirantel, avermectins. They will usually be in powdered or particulate form for use in the present invention.

The bio-erodible matrix is preferably composed of an absorbable or dissoluable polymer or polymers intimately mixed with or coating the medicament. Naturally biologically compatible, non-toxic, non-deleterious materials should be used, and many are known. Typical of the absorbable polymers which can be used as a matrix for the medicament in any of the bolus devices of the invention are the following: poly L(-) lactide, poly (DL) lactide, addition copolymers of lactide and glycolide (U.S. Pat. No. 4,137,921), random copolymers of lactide and glycolide, poly-p-dioxanone, addition and random copolymers or blends of p-dioxanone and any of the preceding lactones or other bio-erodible polymeric material. The major requirement is that the polymers be slowly absorbed or dissolved in body fluids so that they will continuously expose new surfaces containing the medicament as they slowly erode and release the medicament particles into the fluids in the rumen over a long period of time. Naturally proper concentrations of medicament must be used.

The medicament-containing matrix portion of the boluses may be formed by a variety of means known to the plastics and polymer fields, such as extrusion, injection molding, compression molding or insertion molding, etc. The absorbable polymer may comprise from about 10 to about 90 percent by weight of the bio-erodible matrix and the medicament may comprise the remaining 90 to 10 percent by weight thereof. No additional fillers or binders are necessary, but they may be included to improve processing.

The medicament-containing bio-erodible matrix may be placed around a heavy metal inner core, which core may be in one piece or in segments. It has been found that where the boluses have sufficient weight, they will be rumen-retentive for at least two weeks and usually much longer. In addition to the various retention means used, i.e., to having the device be of sufficient weight, sufficient density, or undergo a change of conformation so that it is retained within the rumen for long periods of time, it is necessary to insure that the medicament to be dispensed actually remains in the rumen. Because the medicament is in a bio-erodible matrix which does not necessarily dissolve evenly, it was found that large chunks of the medicament-containing bio-erodible matrix could break off periodically and be lost from the rumen. By encasing the device within one or more meshes, i.e., a perforated cover with openings at least 5 microns in diameter, which mesh may be composed of fine wire or other non-absorbable material such as polyester or nylon (or other relatively pliable or flexible material which will remain unabsorbed in the body and retain its integrity for at least a month or two or during the time the medicament is being released), when large chunks of the medicament-containing matrix break off, they will be retained within the mesh and held with the remaining portion of the bolus device and will continue to erode until such time as the erosion or dissolution of the matrix leads to pieces small enough to flow through the mesh apertures. The mesh openings are large enough so that the body fluids can flow through and small enough so that only very small pieces of the matrix will escape undissolved. As can be seen, the release of medicament occurs in a sustained release fashion, but one which can differ slightly from bolus to bolus. The mesh can be best used as a tubular mesh, so only the two ends need be closed, sewed, clipped, tied or otherwise fastened to encase the bolus.

BRIEF DESCRIPTION OF THE DRAWINGS

FIGS. 1-4 represent three variations of the simplest form of the bolus of the present invention.

FIG. 1 is a perspective view of the exterior of the bolus, which exterior is common to the variations of FIGS. 2, 3, and 4.

FIGS. 2, 3, and 4 are cross-sectional views taken across Line 2—2 of FIG. 1, and depict three variations of the interior of the bolus of FIG. 1. FIG. 3 contains a cut-away view of the interior just below the cross-section.

FIG. 5 is a perspective view of another embodiment of the bolus of the present invention, depicted in its open position, such as it might be in after administration into the rumen.

FIG. 6 is a cross-sectional view taken along Line 6—6 of FIG. 5, with a cut-away view of parts of the interior just below the cross-section.

FIG. 7 is a perspective view of the bolus of FIG. 5 in its folded position, placed inside of a gelatin capsule, such as it would be in prior to being administered to a ruminant. FIGS. 8 and 10 are perspective views of two different variations of another embodiment of the bolus of the present invention, shown in the open position, such as could be found in the rumen after the bolus had been administered. FIGS. 11 and 9 are perspective views of the boluses of FIGS. 8 and 10 respectively shown inside of a shape holding means prior to administration.

DETAILED DESCRIPTION OF THE INVENTION

As illustrated in FIGS. 1-4, the simplest form of the rumen-retention bolus of the present invention is in the shape of a cylinder 10 having as the retention means, a heavy metal rod 12 as its inner core, which rod can either be centrally located as shown in FIG. 2, or be located at one end only as shown in FIG. 3, or be in two pieces located at each end of the cylinder as in FIG. 4. The inner core heavy metal rod 12 is surrounded by an outer core of an absorbable polymer matrix 14 containing admixed therein particles of medicament 16, and which outer core cylinder surface 18 is surrounded on all sides by a sleeve-like, fine, polyester mesh 20. The polymer matrix containing particles of medicament, while shown in the cut-away in FIG. 3, is the same in FIGS. 2 and 4, where there is no metal rod.

As illustrated in FIGS. 5-7, the most preferred bolus of the present invention can have two semi-cylindrical segments 22 formed from an absorbable polymer matrix 14 containing admixed therein particles of medicament 16, which semi-cylindrical segments are each surrounded by a sleeve-like, polyester mesh 20 and which segments are joined by a coiled steel spring 30 which has been partly imbedded into each of the segments 22 as the retention means. In FIG. 6, the cross-sectional view of the bolus of FIG. 5 can be seen and in the cut-away portion, the polymer matrix containing medicament particles can be seen. FIG. 7 shows the bolus of FIGS. 5 and 6 with the two semi-cylindrical segments 22 folded to somewhat resemble the bolus of FIG. 1, and in order to keep it in its folded position so that it would fit in a bolling gun, it is inside a gelatin capsule 32 which is the dissoluable shape holding means. The bolus of FIG. 7 is administered to a ruminant via a bolling gun, and a short time after reaching the rumen, the gelatin capsule dissolves and the tension of the coiled spring 30 (which is the flexible resilient means) forces the two segments 22 open so that the bolus assumes the shape as shown in FIG. 5.

FIGS. 8 and 11 illustrate another embodiment of the invention wherein two circular cylindrical segments 40, formed from an absorbable polymer matrix containing admixed therein medicament particles (just as shown in FIG. 1), which segments are each surrounded by a sleeve-like, polyester mesh 20, and which are joined at their outer ends by an elastomeric band 42. In FIG. 11, the two segments 40 are positioned to form a cylindrical shape with the elastomeric band 42 under tension and are held in that position by being encased in a gelatin capsule 32. FIG. 8 illustrates the position the bolus might assume in the rumen after the bolus has been administered to an animal and the gelatin capsule 32 of FIG. 11 has dissolved and the elastomeric band (which is the flexible, resilient means) 42 has, by means of its tension, forced the bolus to assume a different shape than in FIG. 11.

Optionally, the segments 40 may contain a metal core, such as a circular steel rod, as shown in FIGS. 2-4, if desired. Also, instead of just two segments, as depicted in FIGS. 8 and 11, there can be more, for example, three or four segments work well, with or without any metal core inside the various segments.

FIGS. 9 and 10 illustrate a four-segmented bolus, wherein the segments 50 are connected in chain fashion by means of the mesh 20, which surrounds all the segments, with the two chain end segments being connected by an elastomeric band 42. FIG. 9 shows the bolus of FIG. 10 as it will be in the bolling gun at the time of administration, where it has a water-soluble coating 52 applied as the shape-holding means to help it retain its shape. FIG. 10 shows the bolus configuration of FIG. 9 as it will exist in the rumen after the water-soluble coating 50 has dissolved and allowed the elastomeric band 42 to change the configuration of the bolus segments. The absorbable polymer matrix containing admixed therein medicament particles is present in the bolus of FIG. 10, but it is not specifically depicted, being very similar to what is depicted in FIGS. 3 and 6.

The Drawings are intended to show usable embodiments, but obviously many changes are possible, i.e., a semi-circular rod or cylinder does not have to be exactly semi-circular or exactly cylindrically shaped, and many obvious equivalents will be immediately apparent to those skilled in the art.

The bolus described is particularly useful in administration of anthelmintics such as mebendazole and levamisole providing sustained release of these medicaments for periods of thirty days or longer, as desired.

Other anthelmintics can also be utilized. Examples are: other benzimidazoles (albendazole, cambendazole, fenbendazole, parbendazole, oxfendazole, oxybendazole, thiabendazole, etc.), organophosphates (trichlorfon, etc.), pyrazino-isoquinolines (praziquantel), piperazines, other phenyl imidazoles, carbamates, and other anthelmintics such as morantel, pyrantel, avermectins, etc. Other medicaments may be used. This technology could also be of use for treatment of animals with:

antibiotics, such as antimicrobials or growth promoters
sulphas
cocidiostats
steroids and other anti-inflammatories
vitamins, minerals and microelements
antiprotozoans, in general
insecticides
contraceptives
tickcides and therapy of mange
antidiarrheals
control of vampire populations.

The absorbable polymers used as the bio-erodible matrix for the medicament in any of the device may be chosen from any of the following: poly L(-) lactide, poly(DL) lactide, addition copolymers of lactide and glycolide (U.S. Pat. No. 4,137,921 and other pending), or random copolymers of lactide and glycolide. Poly p-dioxanone, addition and random copolymers or blends of p-dioxanone and any of the other preceding lactones are especially useful.

The following examples show how to make the boluses of the present invention.

EXAMPLE 1

Dry particles of p-dioxanone polymer are measured into a container with 33 wt. percent levamisole HCl and mixed by tumbling for two hours. The dry polymer-drug mixture is stored at room temperature under vacuum of 0.1 mm or better. The mixture is charged into a helicone mixer and maintained at 0.1 mm at least one hour. The vacuum is released with dry nitrogen and the components are heated to about 135° C. with mixing. The molten blend is forced with nitrogen pressure into a cylindrical mold containing a ¼" stainless-steel rod and allowed to cool. The bolus is trimmed and covered with a knitted Dacron polyester mesh having pores about 0.8 mm by 1.6 mm. The finished boluses weighed 17.7 g average. They are like those in FIGS. 1 and 2.

EXAMPLE 2

Dry particles of 65/35 lactide glycolide copolymer and 16 wt. percent mebendazole are treated as in Example 1. The dry mixture is charge into a helicone mixer, maintained at 0.1 mm for 1 hour and heated to 160° C. under nitrogen with stirring. The boluses are molded and covered with Dacron polyester mesh as in Example 1 using 5/16" metal cores. Boluses weighed about 20 g.

EXAMPLE 3

The process of Example 1 is followed except the core is ⅜" steel rod, the polymer L(−) lactide and the drug 16 wt. percent mebendazole. Finished boluses weighed about 18 g.

EXAMPLE 4

The process of Example 1 is followed where the core is 5/16" steel, the polymer 65/35 random lactide/glycolide copolymer and the drug 16 wt. percent each levamisole HCl and mebendazole. Finished boluses weighed about 22 g.

EXAMPLE 5

The process of Example 1 is followed where the core is ¼" steel rod, and the matrix is an inner layer of poly-p-dioxanone with 16 wt. percent levamisole and an outer layer of 65/35 random lactide/glycolide copolymer with 16 wt. percent mebendazole. Finished boluses weighed about 22 g.

EXAMPLE 6

The process of Example 1 is followed where the core is ¼" steel rod, the polymer matrix is equal parts of poly-p-dioxanone and 65/35 random lactide/glycolide copolymer and the drug is 30 wt. percent levamisole. Finished boluses weighed about 18 g.

EXAMPLE 7

The polymer-drug mixture in Examples 1-6 is discharged, ground and dried. It is charged into an injection molding machine and formed into a solid rod with a concentrically-placed metal core of 5/16" diameter steel or iron rod adout 1-½" long.

EXAMPLE 8

The polymer-drug mixtures described in Examples 1-6 are treated as in Example 7, but molded into segments about 0.5 inches in diameter and 0.5 inches long. The segments are fitted into a Dacron polyester mesh tube, fastened off between the segments and at the end. A segmented polyether polyurethane band is fixed to both ends of the device and the whole is covered with a water-soluble film such as gelatin or hydroxypropyl cellulose. A solid rod about 0.5 inches in diameter and 1-2.5 inches long is formed depending on the number of segments used. They are like those in FIGS. 8-11.

EXAMPLE 9

Using any polymer-drug mixture from Examples 1-6, the dried powdered mixture is charged into an injection molding machine. Semi-circular rods are formed with a stainless steel spring interlinking the halves. The whole device is covered with soft Dacron polyester mesh, folded in half to form a solid rod 0.5 inches in diameter and about 2.5 inches in length. The entire device is covered with gelatin or cellulose film. They are like those in FIGS. 5-7.

The foregoing examples illustrate boluses for sheep. Those for cattle are similar but larger. The efficacy of the sustained release boluses was demonstrated by infecting lambs with various worm larvae and administering boluses of varying types, polymer compositions, anthelmintics, and dosages, periodically checking the animal feces and then checking to see if the animal was infected at various times at necropsy. At this time the condition of the bolus was checked. Other animals were X-rayed periodically for the presence of metal-containing boluses. Boluses of varying weights and density were tested. Non-segmented boluses required a heavy metal core, but segmented boluses did not require a metal core to be rumen-retentive. Many boluses were still effective after three months.

We claim:

1. A rumen-retentive bolus comprising a medicament admixed in a bioerodible sustained-release matrix; a mesh made of a nonabsorbable material completely encasing said medicament-containing matrix; retention means to prevent the bolus from being regurgitated by the ruminant in less than two weeks which retention means is to have the medicament-containing matrix contain at least two matrix segments capable of changing their positions relative to each other after administration into the rumen, and wherein at least two of said matrix segments are joined together by flexible resilient means in the form of a coiled spring, so that the bolus segments can be formed into a shape suitable for administration from a bolling gun, and wherein dissolvable shape holding means are used to keep it in said shape until after it has been administered into the rumen and the shape holding means dissolved by the ruminal fluids, whereupon the bolus changes its shape to become sufficiently large that it cannot be regurgitated.

2. The bolus of claim 1 wherein the sustained release matrix is made from the absorbable polymer, poly p-dioxanone.

* * * * *